US005993626A

United States Patent [19]

Landers et al.

[11] Patent Number: 5,993,626

[45] Date of Patent: Nov. 30, 1999

[54] CAPILLARY ELECTROPHORESIS OF TRANSFERRIN GLYCOFORMS

[76] Inventors: James P. Landers, 923 7th Ave., Rochester, Minn. 55904; Rajani Prasad, 14205 Canterbury Ct., Leawood, Kans. 66224; Robert P. Oda, R.R. 1, P.O. Box 855, Stewartville, Minn. 55976; Robert L. Stout, 10521 Bradshaw St., Overland Park, Kans. 66215

[21] Appl. No.: 08/788,323

[22] Filed: Jan. 24, 1997

[51] Int. Cl.$^{6}$ ........................ G01N 27/26; G01N 27/447

[52] U.S. Cl. ........................ 204/451; 204/454; 204/455; 204/601; 204/605

[58] Field of Search .................................. 204/601, 602, 204/603, 604, 605, 451, 452, 453, 454, 455

[56] References Cited

U.S. PATENT DOCUMENTS 5,545,302 8/1996 Zhu et al. .............................. 204/454

FOREIGN PATENT DOCUMENTS 0 442 177 B1 3/1994 European Pat. Off. .

OTHER PUBLICATIONS

Ferenc Kilar and Stellan Hjerten, "Fast and high resolution analysis of human serum transferrin by high performance isoelectric focusing in capillaries" Electrophoresis, vol. 10 No month available (1989) 23–29.

John P. Allen et al, "Carbohydrate–Deficient Transferrin as a Measure of Immoderate Drinking: Remaining Issues" Alcoholism: Clinical and Experimental Research; vol. 18, No. 4 (Jul./Aug. 1994) 799–812.

Anton et al., Clin. Chem., 40(3):364–368 No month available (1994).

Bean et al., Alcoholism Clin. Exp. Res., 17:1163–1170 No month available (1993).

Grant et al., Alcohol Health Res. World, 15(1):91–96 No month available (1991).

Hempe et al., Clin. Chem., 40/12:2288–2295 No month available (1994).

Kilar et al., Electrophoresis, 10:23–29 No month available (1989).

Kilar et al., Journal of Chromatography, 480:351–357 No month available (1989).

Landers, Clin. Chem., 41/4:495–509 No month available (1995).

Stibler et al., Acta Medica Scand., 204(1–2):49–56 No month available (1978).

Stibler et al., Acta Paediatr. Scand. Suppl., 375:21–31 No month available (1991).

Stibler et al., Acta Paediatr, 82:55–59 No month available (1993).

Stibler et al., Alcoholism Clin. and Exp. Res., 10(5):535–544 No month available (1986).

Stibler et al., Pharmacology, Biochemistry & Behavior, vol. 13, Suppl. 1, pp. 47–51 No month available (1980).

van Eijk et al., Clin. Chim. Acta, 165:141–145 No month available (1987).

van Eijk et al., J. Clin. Chem. Clin. Biochem., 14:475–478 No month available (1976).

Yan Xu, Analytical Chemistry, vol. 67, No. 12, pp. 463R–473R (Jun. 15, 1995).

Oleg Iourin et al, "The identification of abnormal glycoforms of serum transferrin in carbohydrate deficient glycoprotein syndrome type I by capillary zone electrophoresis" Glycoconjurate Journal, 13, pp. 1031–1042, No month available 1996.

Ferenc Kilar et al "Unfolding of human serum transferrin in urea studied by high–performance capillary electrophoresis," Journal of Chromatography, 638, pp. 269–276, No month available 1993.

Robert P. Oda et al, "Effect of cationic buffer additives on the capillary electrophoretic separation of serum transferrin from different species", Electrophoresis 17 pp. 431–437, No month available 1996.

Ference Kilar et al, "Separation of tryptophan–derivative enantiomers with iron–free human serum transferrin by capillary zone electrophoresis" Electrophoresis 16 pp. 1510–1518, No month available 1995.

*Primary Examiner*—William H. Beisner
*Assistant Examiner*—John S. Starsiak, Jr.
*Attorney, Agent, or Firm*—Thorp Reed & Armstrong, LLP

[57] ABSTRACT

A capillary electrophoresis method for resolving transferrin glycoforms in a sample is described. The capillary comprises a lumen, an inlet and an outlet. The lumenal surface of the capillary is charge-neutral and the capillary contains a buffer containing a polymeric matrix. The transferrin sample is contacted with the inlet of the capillary. A voltage is applied to the capillary such that the inlet is a cathode and the outlet is an anode and such that the voltage is effective for resolving transferrin glycoforms. A method for diagnosing chronic alcoholism or carbohydrate-deficient glycoprotein syndrome using CE to resolve abnormal populations of transferrin glycoforms is also described.

16 Claims, 3 Drawing Sheets

Densitometric Scan Resulting from Gel Electrophoresis

CAPILLARY ELECTROPHORESIS OF TRANSFERRIN GLYCOFORMS

FIELD OF THE INVENTION

This invention relates to a capillary electrophoresis method for resolving transferrin glycoforms in a sample, and to resolving and detecting transferrin glycoforms that are indicative of pathologic states, such as chronic alcoholism and carbohydrate-deficient glycoprotein syndrome.

BACKGROUND OF THE INVENTION

The glycoprotein transferrin (Tf) is the primary iron-transport protein in human plasma. Tf plays an important role in directing plasma iron to bone marrow for incorporation into developing reticulocytes. Tf consists of a single polypeptide chain of 679 amino acids with two potential sites for glycosylation, and has a molecular weight of 79,570 Daltons.

Human Tf is microheterogenous with respect to its glycosylation. Nine glycoforms of Tf, referred to as sialoforms, can exist, varying in the number of sialic acid residues bound to the surface glycans. The tetrasialoform is found at the highest concentration in normal human serum, with the hexa-, penta-, and tri-sialoforms detectable at lower concentrations. The di-, mono-, and asialoforms, collectively referred to as "carbohydrate-deficient transferring" (CDT's) are observed only under certain pathological conditions, including patients chronically consuming excessive amounts of alcohol and in patients having "carbohydrate-deficient glycoprotein syndrome (CDGS)," which is manifested by severe neurological deficiencies.

Capillary electrophoresis (CE) is a technology useful for the analysis of a variety of analytes of basic scientific and clinical importance. CE involves the electrophoretic separation of analytes, typically in narrow-bore fused silica capillaries. The capillaries employed in CE provide a high surface-to-volume ratio which allows for very efficient dissipation of Joule heat generated from large applied fields. Other techniques operating on this principle are known in the art, such as the use of capillary-like microchannels or troughs etched in glass chips or other materials to form microfabricated devices. As used herein, the term "capillary" refers to such microchannels or troughs in such devices, and the term "capillary electrophoresis," or "CE," refers to techniques and systems employing such microchannels, troughs, or devices.

Electrophoretic separations can be easily performed at up to 30,000 volts while the capillary remains close to ambient temperature. This permits "minute" time-scale separations and a significant reduction in analysis time in comparison to slab gel electrophoresis. Moreover, it is well established that both the speed of the separation as well as the resolution of the components are a direct function of the applied electric field in electrophoresis. Using applied electric fields up to 100 times those typically used with conventional electrophoretic methods, CE usually outperforms slab gel electrophoresis, not only in speed of analysis, but also in resolution.

In addition, the microliter column volume (e.g., 0.92 $\mu$l for a 47 cm×50 $\mu$m capillary) used in CE provides other advantages including relatively low amounts of reagent and sample consumed and the speed at which the capillary can be regenerated for subsequent analyses.

CE thus provides rapid (minute time-scale), high efficiency ($10^5$–$10^7$ theoretical plates/m), reproducible (relative standard deviation<1%), automated separations on low volume samples under native or denaturing conditions, all of which provide distinct advantages over conventional slab gel electrophoresis.

A number of modes of CE have developed in the art, including capillary zone electrophoresis (CZE; separation in low ionic strength buffer), capillary isoelectric focusing (CIEF; separation of proteins in a pH gradient of ampholines) and capillary gel electrophoresis (CGE; separation in a polymeric sieving matrix).

Although CE provides efficient, reproducible and automated separation, the successful and reproducible CE separation of proteins, and especially of protein isoforms having virtually identical molecular weights, is problematic. Proteins have an intrinsic tendency to interact not only with other proteins, but also with the capillary wall. Certain proteins have been successfully separated using CE, but there is no universal approach or set of conditions applicable to all target proteins. A CE system able to separate a target protein from other components in a sample solution or to resolve clinically significant isoforms of a target protein within a sample solution would be an attractive alternative to less efficient and reliable methods in developing an assay for such protein or proteins.

Analysis of human Tf by CIEF and CZE has been reported in the literature. Each of these approaches, however, has disadvantages in the context of achieving a useful clinical assay. CZE relies solely on mass-to-charge ratios for separation and, therefore, slight differences in mass or charge may not be adequate for resolution. CIEF can effectively separate Tf isoforms based on differences in their individual pI's, but separation takes too long to be a viable means of efficiently handling a large number of samples.

Methods currently available in the clinical setting for discriminating Tf glycoforms include isoelectric focusing in slab gels followed by visualization of immunofixed glycoforms, immunopurification followed by isoelectric focusing and protein staining, and anion exchange with immunological detection of subfractions of Tf's at precisely controlled pH (5.65). In the latter method, CDT's are poorly retained by the column and are separately measured by radioimmunoassay (RIA).

While these methods function adequately for the analysis of serum Tf, they would be prohibitively expensive (reagent and labor costs) for handling a large number of samples in a high throughput manner (e.g., several hundred per day) and are not amenable to automation.

There is currently no automated assay available for the diagnosis of chronic alcoholism or CDG syndrome or for the resolution of Tf glycoforms generally. It would be highly advantageous to provide a system for resolving Tf glycoforms that would be amendable to automation and be capable of rapidly analyzing samples in a high throughput manner. The desirable assay would be capable of rapidly detecting Tf glycoforms indicative of pathologies characterized by the presence of CDT's.

SUMMARY OF THE INVENTION

In general, the present invention features a capillary electrophoresis method for resolving transferrin glycoforms in a sample. In one embodiment of the invention, a capillary comprises a lumen, an inlet, and an outlet. The lumenal surface of the capillary is charge-neutral and the capillary contains a buffer that includes a polymeric network. The sample is contacted with the inlet of the capillary. A voltage is applied to the capillary such that the inlet is a cathode and the outlet is an anode and such that the voltage is effective for resolving transferrin glycoforms.

The method of the invention may further include detecting resolved transferrin glycoforms in the sample. The resolved transferrin glycoforms may be detected by measuring the absorption of light at between about 200–280, preferably 200 or 214, nanometers by the sample components in the capillary at a position in the capillary where the transferrin glycoforms have been resolved.

In preferred embodiments of the invention, detected Tf glycoforms may be correlated with a pathologic state. For example, detected Tf glycoforms may be correlated with chronic alcoholism in a patient, where the capillary electrophoresis method is performed on a sample of immunopurified Tf from the patient or on a sample of patient serum. Similarly, detected Tf glycoforms may be correlated with carbohydrate-deficient glycoprotein syndrome in a patient, where the capillary electrophoresis method of the invention is performed on a immunopurified Tf or serum sample from the patient.

In preferred embodiments of the invention, a fused silica capillary is used. The capillary may also be formed from a glass or plastic material. Where the capillary comprises fused silica, the lumenal surface of the capillary may include a coating, such as dimethylpolysiloxane, to render the lumenal surface charge-neutral. The capillary, whether or not precoated with dimethylpolysiloxane, may be also coated with a nonionic detergent, such as Brij 35, prior to use.

In preferred embodiments, the polymeric network in the capillary is free-flowing, comprising linear, non-crosslinked polymers. A free-flowing polymeric network is one that is "pump-able," i.e., it can be pumped into a capillary, used in an assay, and pumped out of the capillary after use. The buffer may comprise a network of methyl cellulose in a borate buffer. Where methyl cellulose is used, it is preferably present at a concentration of about 0.4 to about 0.5% (w/v), and has an average molecular weight of between about 17.5 kilodaltons (kD) and 86 kD. Other suitable polymeric networks include linear, branched, non-crosslinked polymers.

As described herein, the invention has numerous advantages. The capillary electrophoresis method described herein permits rapid and reproducible resolution of Tf glycoforms from patients. The invention is amenable to low volume high throughput testing of patient samples in the clinical laboratory, and provides a useful screen for CDGS and chronic alcoholism. The use of the invention in screening Tf of chronic alcoholism patients provides a very valuable tool in the assessment and management of such patients. For example, the CE method of resolving Tf glycoforms may be performed on samples from chronic alcoholism patients in therapy to determine whether such patients have chronically consumed excessive amounts of alcohol during therapy. The CE method for resolving Tf glycoforms as described herein is amenable to automation, and the capillary used in the system may be recycled, i.e., washed and used in repeated assays.

Other features and advantages of the invention will be apparent from the following description, including the drawings, and from the claims.

DETAILED DESCRIPTION OF THE INVENTION

Figure 1:
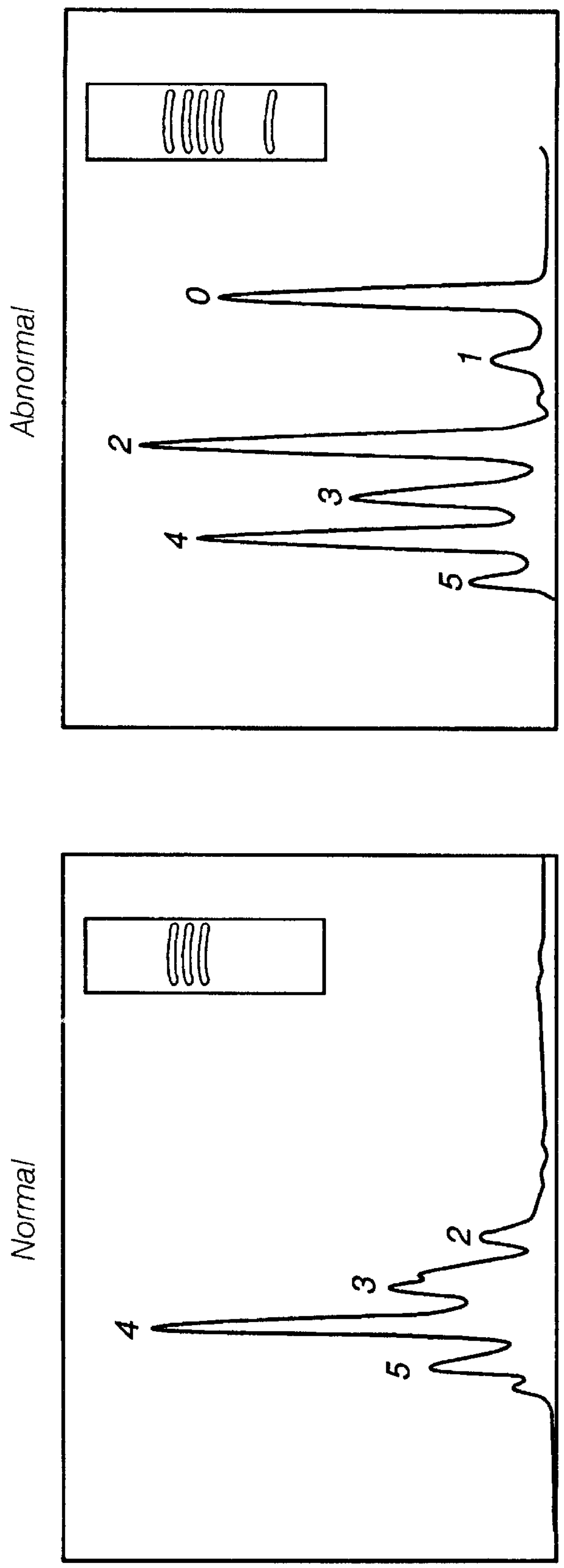
FIG. 1 is a graphic depiction of the Isoelectric focusing gel -resolved Tf glycoforms of immunopurified Tf from serum of normal and abnormal (CDGS) human patients. Each panel shows a densitometric scan of the gel shown in the inset. The scan of the abnormal sample shows elevated a-, mono-, and di-sialo Tf (labeled 0, 1, and 2 in the Figure.)

The present invention relates to a CE method for resolving Tf glycoforms. In one embodiment, the invention provides a highly advantageous assay scheme for resolving and detecting Tf glycoforms indicative of chronic alcoholism, CDG syndrome or any other pathologic state characterized by abnormal populations of Tf glycoforms and in particular increased concentrations of the lower sialoforms. This assay scheme is amenable to automation and allows rapid analysis of samples in a high throughput manner compatible with a clinical laboratory setting. Resolution of Tf glycoforms using CE provides a major advance in diagnosing pathologies related to abnormal populations of Tf sialoforms.

In CE, the physical characteristics of the capillaries are important factors in resolving the components of interest in a sample. The capillaries employed in CE are typically <100 $\mu$m internal diameter (i.d.) and 20–100 cm in length, although the capillaries suitable for use in the present invention are not necessarily limited to these dimensions. In a preferred embodiment, Tf glycoforms are resolved using a capillary that is about 50 $\mu$m i.d. and about 27 cm in length.

The capillary of the present invention comprises a lumen having a lumenal surface, an inlet, and an outlet. The capillary may be a fused silica capillary, or it may be a channel of appropriate dimensions formed from any suitable material, such as silica, plastic, or glass. The lumen is a bore or a channel through the capillary in which the sample, e.g. Tf glycoforms, can pass in order to be resolved. In general, any capillary, or capillary-like channel or trough in any microfabricated device is suitable for use in the present invention. Components in the lumen such as matrices, buffers and ampholines allow the sample to be resolved upon application of an electric field.

Capillaries used in CE may be comprised of fused silica, which is known to impart a net negative charge to the inner surface of the capillary. The inner surface of the capillaries may in this case be coated with polymers or other compositions which result in a surface with the desired charge characteristics, e.g. charge-neutrality. Capillaries formed from other materials besides fused silica, such as plastic, may also be used. This may alleviate the necessity coating of the lumenal surface to achieve the desired charge characteristics. In addition, an external polymeric coating is used which produces a surprisingly flexible narrow-bore capillary that would otherwise be extremely fragile.

In the present invention, the lumenal surface of the capillary preferably is neutral with respect to charge. As stated above, the typical commercially available fused silica capillaries are negatively charged at their surfaces and, therefore, must be neutralized. Charge-neutrality of the lumenal surface may be achieved using a number of different approaches. For example, a capillary made from a material that is neutral with respect to charge may be used. This avoids the necessity for providing a coating of the lumenal surface. Alternatively, the lumenal surface of the capillaries may be coated with a composition that results in a charge-neutral capillary lumenal surface. A wide variety of compositions may be used to coat fused silica capillaries to attain charge-neutrality. In addition, a number of fused silica, charge-neutral, coated capillaries such as DB-1 (dimethylpolysiloxane), DB-5, or DB-17 coated capillaries are commercially available from J&W Biochemicals, Folsom, Calif. In one preferred embodiment, a capillary coated with DB-1 is used. In one preferred embodiment a DB-1 coated capillary is precoated with the non-ionic detergent Brij 35 to further reduce electroosmotic flow.

Separation of the Tf glycoforms requires the presence within the lumen of the capillary of an appropriate buffer containing a polymeric network. The buffer provides an environment that is chemically compatible for the separation of the glycoforms, and also acts as the solvent for the polymeric matrix. The combination of the charge neutral lumenal surface and the buffer containing the polymeric network may provide for the separation of molecules by two different mechanisms. While not bound by theory, a coating of the wall to provide charge neutrality, may provide insulation of the analyte from the charged surface, and may provide a viscous layer to reduce electroosmotic flow (EOF) at the lumenal surface-solution interface. The reduction in EOF may allow the separation of the glycoforms by virtue of the differences in their charge-to-mass ratio. The polymeric network may also provide a sieving medium, by which molecules having similar charge-to-mass ratios may be separated by their mass-equivalent hydrodynamic volume. Either mechanism individually, or the combination of the two mechanisms, may effect the resolution of the Tf glycoforms.

The polymeric network can either be a network polymerized within the capillary or a free-flowing network. A free flowing network, as noted above, is pump-able into and out of the capillary, as opposed to a gel or matrix that is fixed within the capillary and suitable for single use. Polymerized linear matrices such as linear polyacrylamide may be used as a polymeric matrix, or as a coating. Capillaries coated with linear polyacrylamide or containing cross-linked acrylamide are presently commercially available.

A variety of free-flowing polymeric networks may be used. Free-flowing matrices comprised of cellulosic material are preferred in the present invention. Other free-flowing matrices, such as polyethylene oxide (PEO), polyethylene glycol (PEG), and the linear acrylamides, also may be used. Specifically, cellulosic matrices such as hydroxypropylmethyl cellulose (HPMC), hydroxyethyl cellulose (HEC) or methyl cellulose may be used at varying concentrations. In a preferred embodiment, methyl cellulose at a concentration of 0.5% is used.

The polymeric network is typically suspended in a biological buffer. Selection of a buffering system is a crucial step in devising a separation scheme. The buffering system must maintain the pH compatible for the separation of Tf glycoforms. Furthermore, at similar pH's a particular buffering system results in successful separation, while others may not. Thus, selection of a buffering system is a key step for successful resolution of the components of interest.

The buffering system in the present invention is a borate buffer. In preferred embodiments, a borate buffer, prepared from a combination of boric acid and sodium tetra borate, at about 100 mM concentration and at about pH 8.5, is used.

A Tf or serum sample is contacted with the inlet of the capillary filled with the borate buffer and the sieving matrix. The sample may be applied to the inlet by pressure or electrokinetic injection and may be serum from a patient or purified Tf. Typically, immunopurified Tf from serum that contains all the unresolved Tf glycoforms is applied to the capillary inlet. A Tf sample purified by other techniques can also be used. Furthermore, a sample of serum may also be contacted with the inlet where the capillary comprises a means for purifying the Tf from the serum. For example, Tf may be extracted from serum using a resin-bound antibody housed at the inlet of the capillary. In either case, all the glycoforms of Tf should be separated from other serum components prior to resolution of the individual Tf glycoforms in the capillary.

The sample may be introduced into the inlet of the capillary by various techniques. The most commonly used techniques are electrokinetic injection or hydrodynamic injection. In electrokinetic injection, a low voltage is used initially to allow the sample to enter into the capillary, whereas in hydrodynamic injection, pressure or suction is used to drive the sample into the capillary. The preferred embodiment of the present invention uses electrokinetic injection to introduce the sample for about 20 sec at 6 kV; however, hydrodynamic injection may also be used.

A unique feature of the capillary electrophoresis system in the present invention is that the polarity of the system is reversed from that typically employed in capillary electrophoresis protein separations. Normally, for protein separation the inlet acts as the anode and the outlet as the cathode. In the present invention, however, the capillary is oriented such that the inlet is the cathode and the outlet is the anode.

Additional parameters for electrophoresis include maintaining the capillary temperature at about 20–40° C. This can only be accomplished in CE when large electric fields are applied because the capillary provides a high surface-to-volume ratio which allows for very efficient dissipation of Joule heat.

Separation of the glycoforms of Tf is accomplished by applying a sufficiently high voltage to the capillary such that the glycoforms of Tf are resolved. A voltage of about 20 kV is typically sufficient and preferred, but voltages ranging from 10–30 kV can be used. Such high voltages are required for proper resolution of the Tf glycoforms. The use of a substantially lower voltage may result in poorer resolution of the Tf glycoforms and longer run times. Furthermore, the use of a substantially higher voltage may reduce the run time even further but may also result in poorer resolution due to exceeding the capillary thermostatting capacity of the system.

Detection of the resolved glycoforms may be carried out using a variety of protocols. Typically, a detector is set up to monitor the absorbance at 200 nm or 214 nm, although detection at other wavelengths may be used (e.g. between about 200 nm–280 nm). The detector may be attached at the outlet, or it may precede the outlet. The detector must be attached at a position on the capillary after the position at which Tf glycoforms are resolved. The detection unit may be in the capillary unit, at a point preceding the outlet or end capillary detection and capable of detecting the glycoforms as they migrate towards the outlet. The detector and the accompanying equipment should have the ability to measure migration time, peak areas and heights.

In one embodiment of the present invention, a commercial CE instrument equipped with a UV detector is used. A computer utilizing data analysis software is used for instrument control and data collection. All peak information (migration time, peak areas and height) may be obtained through the software. Examples of commercially available CE instruments include Beckman P/ACE system or a Biofocus 3000 equipped with a 27 cm DB-1 or DB-17 capillary.

An additional advantageous feature of the present invention is the recyclability of the capillary. After evaluation of the first sample, the capillary can be washed out and reused for analysis of additional samples. The capillary may be prepared for the next analysis by washing with two capillary volumes of 20 mM phosphoric acid, one capillary volume of water followed by a 2 minute rinse with fresh separation buffer. The separation buffer contains medium strength borate buffer (approximately 100 mM), pH 8.5, and 0.5% methyl cellulose.

Separation and identification of Tf glycoforms is useful in diagnosing various pathologic conditions. Tf samples obtained from normal human patients contain a large amount of tetrasialoform. Lower concentrations of the hexa-, penta-, and tri-sialoforms are also found. However, serum samples from chronic alcohol abusers contain undersialylated forms of Tf (CDTs). The Tf from alcoholic patients contains detectable amounts of CDT. Specifically, various combinations of elevated di-, mono-, and/or asialoforms of Tf may be observed in alcoholic patients.

The presence of CDT is also seen in patients with CDGS and other pathologic conditions. Thus, the method of resolving the Tf glycoforms in the present invention can be used to detect a number of diseases including alcoholism and CDGS.

In one embodiment of the invention, serum from a patient is collected. Tf glycoforms can, although need not necessarily, be immunopurified from the serum. The sample (purified Tf or serum) is then contacted with the inlet of the capillary containing the buffer and the sieving matrix. The capillary is arranged such that the inlet comprises a cathode and the outlet comprises an anode. A high voltage of about 20 kV is applied to resolve the Tf glycoforms. A detector is attached at a position after the Tf glycoforms have resolved. The presence of a-, mono-, and disialoforms of Tf is indicative of chronic alcohol abuse in the patient. This method also has utility in settings in which the testing of individuals for chronic alcohol abuse is desired, such as testing of transportation workers, military personnel, and the like.

The invention may be illustrated by way of the following examples.

EXAMPLE 1

Immunopurification of Transferrin

A number of protocols are described in the literature for purification of human transferrin. The following protocol describes the methods used for obtaining immunopurified Tf.

Rabbit anti-human transferrin (commercially available from Pierce Biochemical, St. Louis, Mo.) was linked via Schiff base to either Amino link gels following the instructions for the Immobilization Kit from Pierce Biochemicals, Rockford, Ill. or to Sepharose 4B as described by van Eijk et al., *J. Clin. Chem. Clin. Biochem.* 14, 475–78 (1976). 0.3 mL of serum was applied on the affinity column containing immobilized rabbit antitransferrin. After all the serum entered in the column, 0.5 mL of phosphate buffered saline, pH 7.5, (PBS) was applied to the column. After elution of the buffer, 2 mL of PBS was applied to the column. The bottom of the column was immediately capped to prevent further elution. After standing for 10 minutes to allow the transferrin to bind, the column was eluted with 4 to 6 volumes (20 mL) of PBS. The absorbance of the eluate at 280 nm was monitored to ensure complete elution of unbound protein. The transferrin was eluted with 0.1 mol/L glycine HCL pH 2.5. Five 1 mL fractions were collected and spectrophotometrically monitored at 280 nm. The fractions containing the transferrin were pooled and dialyzed against approximately 200 mL of water for 1½ to 2 hours.

Alternatively, the unbound protein can be removed with 25 mM phosphate, 10 mM citrate, pH 7.2, and the Tf eluted with 25 mM phosphate, 10 mM citrate, pH 2.9, followed by dialysis against 50 mM phosphate, pH 7.4, and then against 10 mM borate, pH 8.4.

After dialysis, the sample is centrifuged and the supernatant (approx. 0.5 mL) containing pure transferrin is ready for IEF gel or capillary electrophoresis.

EXAMPLE 2

Separation of Tf Glycoforms Using Slab-Gel Electrophoresis

Current methodology employs slab-gel electrophoresis for resolving the glycoforms of Tf. This Example shows the results of the slab-gel electrophoresis of Tf for comparison with the method of the present invention. Immunopurified Tf (Example 1) from several normal patients and a patient with carbohydrate-deficient glycoprotein syndrome was used.

Separation of Tf glycoforms was carried out on an Isolab Resolve Omega horizontal electrophoresis system with thermoelectric cooling unit and gel surface electrodes using a FB-702 2000 volt power supply. The sample was loaded onto a cooled (8° C.), 13 cm (w) IEF gel (8% polyacrylamide) and voltage applied to focus the sample for 1940 volt hours at 5 constant watts (total time approximately 2 hours). Following the separation, the gel was fixed in 11.5% trichloroacetic acid, 3.46% 5-sulfosalicylic acid for 30 minutes followed by rinsing several times with $ddH_2O$ for 1 hour and finally soaking in $ddH_2O$ for 1 hour. The gel was stained (0.5% Coomassie Brilliant Blue R-250, 25% ethanol, 10% acetic acid) for 1 hour, detained (40% methanol, 10% acetic acid) and soaked in 2.5% (w/v) glycerol for 15 minutes. The dried gel was scanned using a Helena REP system scanning densitometer.

FIG. 1 is a graphic depiction of the resultant densitometer scans from slab gel electrophoresis of Tf immunopurified from the serum of a normal patient and of an abnormal patient. The peaks seen in both panels represent the glycoforms of Tf (protein forms with different amounts of sialic acid attached). The profile on the left (normal) is dominated by the tetrasialo form (labeled 4) with smaller amounts of the penta, tri, and disialo forms. These peaks are obtained by scanning the gel in the inset. The profile on the right shows the presence of significant amounts of the mono and asialo forms, of CDTs (Labeled 1 and 0).

EXAMPLE 3

Separation of Tf Glycoforms Using CE

The method used for separated Tf glycoforms using CE is described below. Serum from normal human patients and patients with CDG syndrome or chronic alcoholism was immunopurified (Example 1) to obtain Tf.

The separation buffer was 100 mM borate, ph 8.5, containing 0.5% methyl cellulose. The borate can be made a number of ways; one such preparation was from 500 mM stock solutions of boric acid mixed with the appropriate amount of 125 mM sodium tetraborate until the desired pH was obtained. All of the buffers were made with Milli-Q (Millipore, Bedford, Mass.) water, and filtered through an 0.2 micron filter (Gelman) before use.

The sample was prepared as described in Example 1 except the dialysis was done against 4 L of 10 mM Borate buffer, pH 8.5.

The capillary electrophoresis assay was done using 50 $\mu$m (id)×27 cm DB-1 coated capillaries which were precoated with Brij 35 and then filled with a separation buffer composed of 0.5% methyl cellulose in 100 mM borate buffer at pH 8.5. After purified serum Tf was electrokinetically injected (20 sec at 6 kV), separation at 20 kV (constant voltage) was carried out for 12 minutes. The capillary may be prepared for the next analysis by washing with two column volumes of 20 mM phosphoric acid, one column volume of water followed by a 2 minute rinse with fresh separation buffer. Other conditions included reversed polarity (inlet as the cathode and the outlet as the anode), the capillary temperature maintained at 20° C., and detection carried out at 214 nm.

CE separation was carried out on a Beckman P/ACE System 2100 equipped with a UV detector. An IBM 486 ValuePoint computer utilizing System Gold software (Beckman Instruments, Fullerton, Calif.) (V.8.1) was used for instrument control and data collection. All peak information (migration time, peak areas and height) was obtained through the System Gold software.

Figure 2:
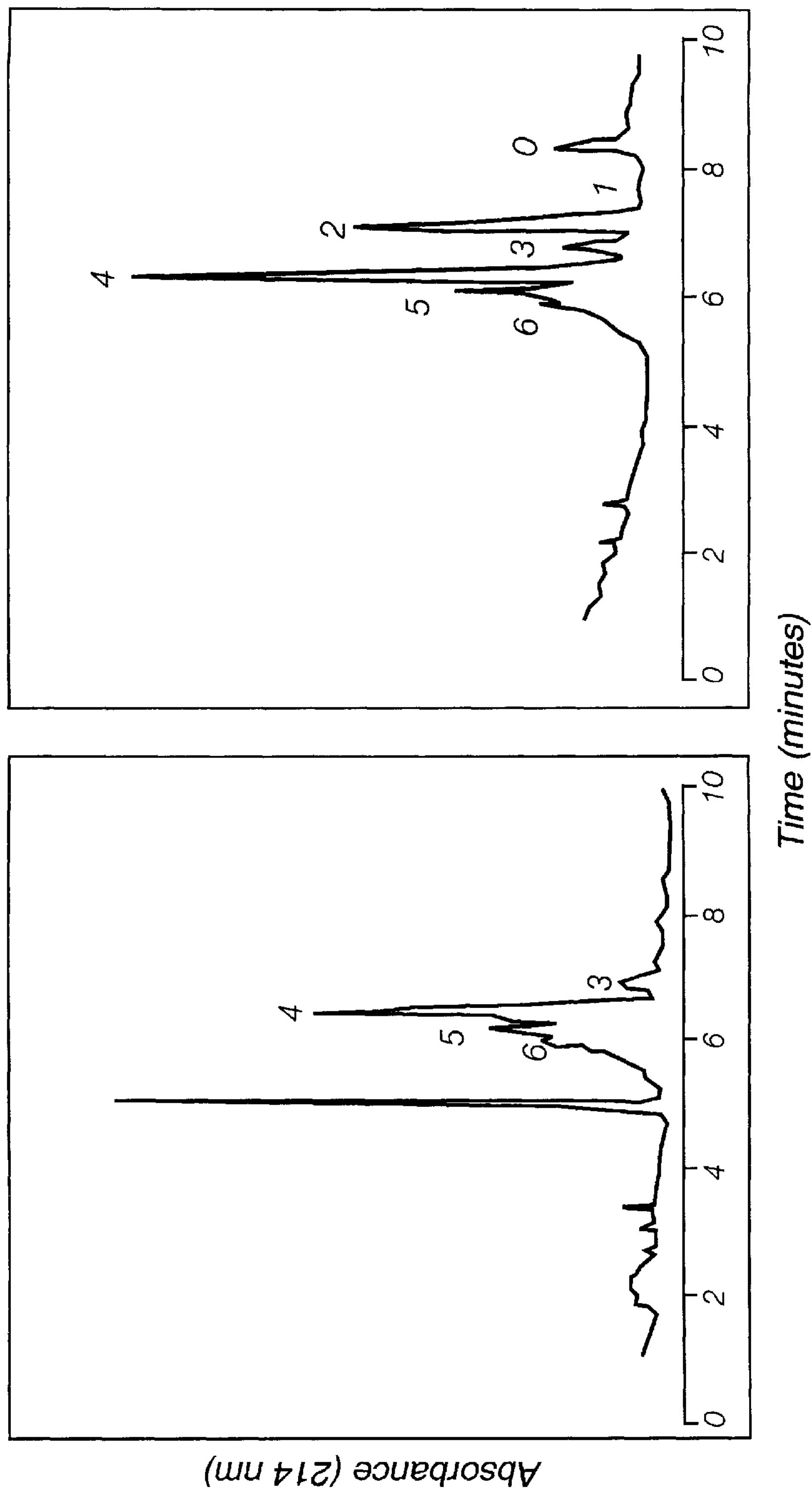
FIG. 2 depicts, in its left panel, the UV absorbance trace obtained from CE separation of normal Tf using the capillary electrophoresis method of the invention. The right panel of FIG. 2 depicts the UV absorbance trace obtained from a CE separation of a patient with CDG syndrome. The elevated a- and di-sialoforms in the right panel are notable (labeled 0, and 2, in the figure and indicated by arrows).

FIG. 2 shows the results from the CE separation of the glycoforms of Tf in sera from a normal human patient and from a patient with CDGS. In the normal patient, a large peak corresponding to tetrasialoform is prevalent. This is consistent with tetrasialoform being the predominant species of Tf in human serum. Small penta-, hexa-, and trisialoform species are also detectable in FIG. 2. All of these are normally found in serum from normal human patients. There are no peaks corresponding to mono-, and asialoforms in normal human serum although a trace of an indication is found at the position corresponding to disialoform Tf.

Figure 3:
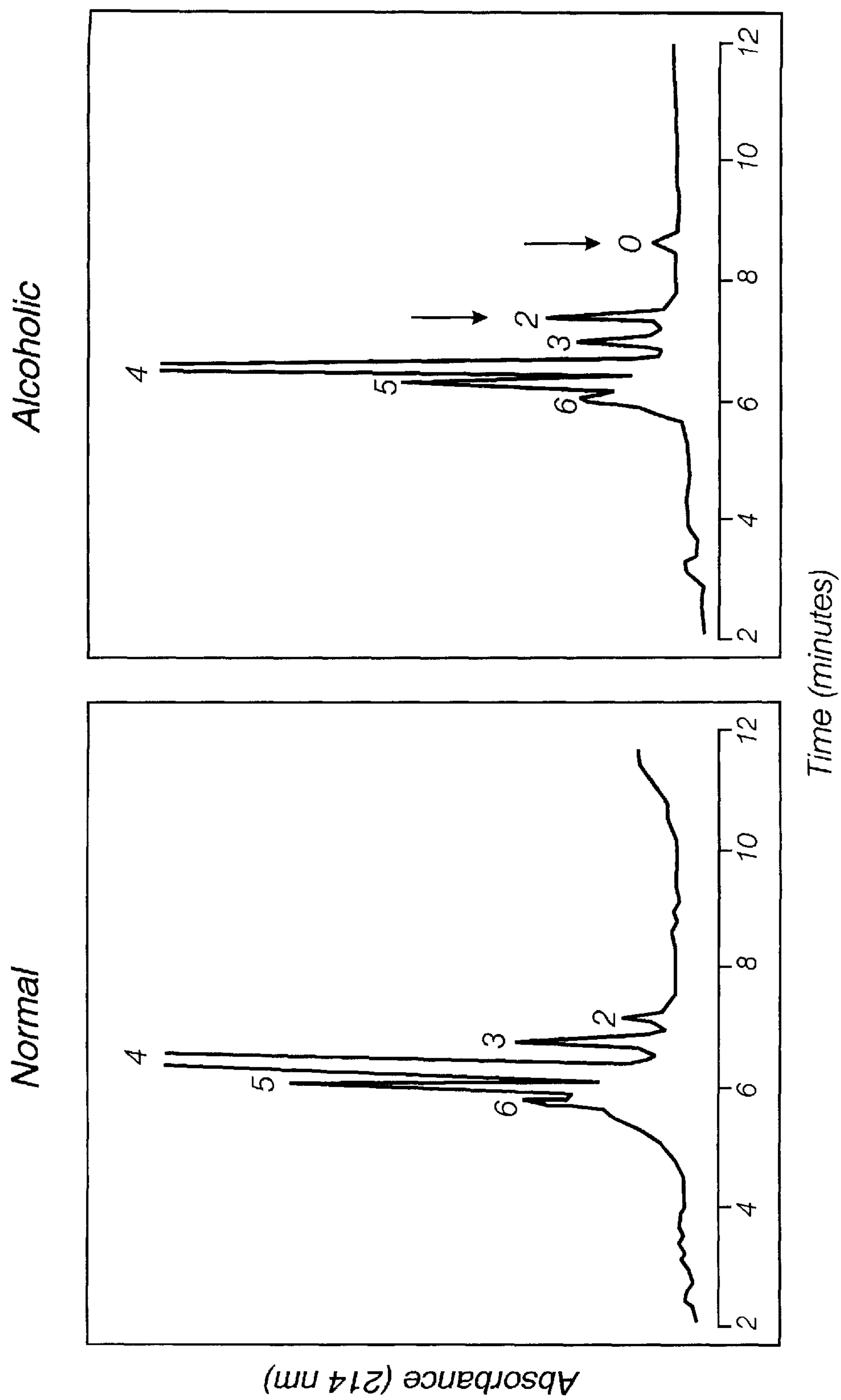
FIG. 3 depicts, in its left panel, the UV absorbance trace obtained from CE separation of normal Tf, and the right panel depicts the UV absorbance trace obtained from a CE separation of Tf from a chronic alcoholism patient. The elevated a- and di-sialoforms (labeled 0, 2 in the figure and indicated by arrows) are notable.

FIG. 2, right panel, depicts the results obtained from separation of Tf glycoforms in the serum of a CDG patient. Again, a peak corresponding to the tetrasialoform of Tf is prevalent. Additional small peaks corresponding to penta-, and trisialoform are also seen. In contrast to Tf from normal human patients, significant peaks are apparent at positions corresponding to di- and asialoforms. FIG. 3 further illustrates that the various glycoforms of Tf present in human serum are clearly resolved using the CE method of the invention.

FIG. 3 depicts results from the CE separation of Tf glycoforms in sera from normal (left panel) and chronic alcoholism (right panel) patients. Tf was immunopurified from serum samples of a normal and a confirmed chronic alcoholism patient as described above. In this figure, the normal sample (left profile) shows the direct on-line detection (no scanning) of the hexa, penta, tetra and trisialoforms. The profile on the right shows detectable amounts of the hexa, penta, tetra and trisialo forms but also the presence of significant amounts of the di and asialoforms. This appears to be characteristic in patients who chemically consume excessive amounts of alcohol.

Other embodiments of the invention are within the scope of the appended claims.

What is claimed is:

1. A capillary electrophoresis method for resolving transferrin glycoforms in a sample, said method comprising:

(a) providing a capillary having a lumen having charge neutral walls, an inlet and an outlet, wherein said capillary contains in the lumen thereof a borate buffer containing a charge neutral polymer comprising cellulosic material;

(b) contacting said inlet of said capillary with said sample; and (c) resolving transferrin glycoforms in order to screen for one or more disorders by applying a voltage to said capillary such that said inlet comprises a cathode and said outlet comprises an anode.

2. The method of claim 1 further comprising detecting resolved transferrin glycoforms in the sample.

3. The method of claim 2, further comprising correlating detected transferrin glycoforms with the presence of a pathologic state.

4. The method of claim 3, wherein said pathologic state is carbohydrate-deficient glycoprotein syndrome.

5. The method of claim 3, wherein said pathologic state is chronic alcoholism.

6. The method of claim 2 further comprising the step of detecting the presence or absence of a-, mono-, or, disialoforms of transferrin in said sample.

7. The method of claim 2 wherein said detecting comprises measuring absorption at about 200 or 214 nanometers of said sample in said capillary at a position on said capillary wherein said transferrin glycoforms have resolved.

8. The method of claim 1 wherein said capillary comprises fused silica.

9. The method of claim 6, wherein said charge neutral walls comprise a coating of dimethylpolysiloxane.

10. The method of claim 9 wherein the lumenal surface of said capillary is further coated with a nonionic surfactant.

11. The method of claim 1 wherein said capillary is formed from a material selected from the group consisting of fused silica, glass, and a plastic.

12. The method of claim 1 wherein said cellulosic material comprises methyl cellulose.

13. The method of claim 12 wherein said borate buffer comprises methyl cellulose in a concentration of between about 0.4% to about 0.5%.

14. The method of claim 1 wherein said cellulosic material is free-flowing.

15. The method of claim 1 wherein said cellulosic material comprises linear, non-crosslinked polymers.

16. The method of claim 1 wherein said voltage comprises about 20 kV.

* * * * *